US011123578B2

(12) United States Patent
Burke-Colvin et al.

(10) Patent No.: US 11,123,578 B2
(45) Date of Patent: Sep. 21, 2021

(54) SKIN CARE FORMULATIONS

(71) Applicant: Mary Kay Inc., Addison, TX (US)

(72) Inventors: Dawn Burke-Colvin, Dallas, TX (US); Michelle Hines, Hickory Creek, TX (US); David Gan, Southlake, TX (US)

(73) Assignee: Mary Kay Inc., Addison, TX (US)

( * ) Notice: Subject to any disclaimer, the term of this patent is extended or adjusted under 35 U.S.C. 154(b) by 0 days.

(21) Appl. No.: 16/556,753

(22) Filed: Aug. 30, 2019

(65) Prior Publication Data

US 2020/0171332 A1 Jun. 4, 2020

Related U.S. Application Data

(63) Continuation of application No. 15/798,944, filed on Oct. 31, 2017, now Pat. No. 10,434,340, which is a continuation of application No. 14/482,053, filed on Sep. 10, 2014, now Pat. No. 9,833,642, which is a continuation of application No. 14/223,729, filed on Mar. 24, 2014, now Pat. No. 8,895,082, which is a continuation of application No. 13/237,573, filed on Sep. 20, 2011, now Pat. No. 8,691,300, which is a continuation of application No. 12/871,557, filed on Aug. 30, 2010, now Pat. No. 8,048,456.

(60) Provisional application No. 61/238,001, filed on Aug. 28, 2009.

(51) Int. Cl.

| | | |
|---|---|---|
| *A61K 36/00* | (2006.01) | |
| *A61Q 1/00* | (2006.01) | |
| *A61K 8/58* | (2006.01) | |
| *A61Q 19/08* | (2006.01) | |
| *A61K 8/9789* | (2017.01) | |
| *A61K 8/64* | (2006.01) | |
| *A61Q 19/00* | (2006.01) | |
| *A61Q 19/02* | (2006.01) | |
| *A61K 8/34* | (2006.01) | |
| *A61K 8/41* | (2006.01) | |
| *A61Q 19/10* | (2006.01) | |

(52) U.S. Cl.
CPC ............... *A61Q 1/00* (2013.01); *A61K 8/345* (2013.01); *A61K 8/41* (2013.01); *A61K 8/585* (2013.01); *A61K 8/64* (2013.01); *A61K 8/9789* (2017.08); *A61Q 19/00* (2013.01); *A61Q 19/02* (2013.01); *A61Q 19/08* (2013.01); *A61Q 19/10* (2013.01); *A61K 2800/85* (2013.01); *Y10S 514/844* (2013.01)

(58) Field of Classification Search
None
See application file for complete search history.

(56) References Cited

U.S. PATENT DOCUMENTS

| | | |
|---|---|---|
| 1,626,814 A | 5/1927 | Goodall |
| 2,798,053 A | 7/1957 | Brown |
| 3,755,560 A | 8/1973 | Dickert et al. |
| 4,421,769 A | 12/1983 | Dixon et al. |
| 4,460,488 A | 7/1984 | Grollier et al. |
| 4,509,949 A | 4/1985 | Huang et al. |
| 4,599,379 A | 7/1986 | Flesher et al. |
| 4,628,078 A | 12/1986 | Glover et al. |
| 4,835,206 A | 5/1989 | Farrar et al. |
| 4,849,484 A | 7/1989 | Heard |
| 5,011,681 A | 4/1991 | Ciotti et al. |
| 5,075,102 A | 12/1991 | Hubaud et al. |
| 5,087,445 A | 2/1992 | Haffey et al. |
| 5,100,660 A | 3/1992 | Hawe et al. |
| 5,215,759 A | 6/1993 | Mausner |
| 5,411,744 A | 5/1995 | Hill et al. |
| 5,720,963 A | 2/1998 | Smith |
| 5,747,538 A | 5/1998 | Meybeck et al. |
| 6,054,296 A | 4/2000 | Bergstrom et al. |
| 6,068,842 A | 5/2000 | Bergstrom et al. |
| 6,090,586 A | 7/2000 | Bergstrom et al. |
| 6,113,914 A | 9/2000 | Lobet et al. |
| 6,143,872 A | 11/2000 | Barbour et al. |
| 6,200,594 B1 | 3/2001 | Ernest et al. |
| 6,203,802 B1 | 3/2001 | Handjani et al. |
| 6,204,018 B1 | 3/2001 | Bergstrom et al. |
| 6,242,012 B1 | 6/2001 | Newmark et al. |
| 6,248,562 B1 | 6/2001 | Dunn et al. |
| 6,254,877 B1 | 7/2001 | De La Poterie et al. |
| 6,290,938 B1 | 9/2001 | Tanner et al. |
| 6,296,849 B1 | 10/2001 | Sadziene et al. |
| 6,300,101 B1 | 10/2001 | Sadziene et al. |
| 6,359,808 B1 | 3/2002 | Chen et al. |

(Continued)

FOREIGN PATENT DOCUMENTS

| | | |
|---|---|---|
| AU | 2004203276 | 2/2005 |
| AU | 2005328670 | 9/2006 |

(Continued)

OTHER PUBLICATIONS

"Beraca launches range of rainforest-sourced actives," *Breaking News on Cosmetics Formulation & Packaging in North America*, Jun. 9, 2005, retrieved on Nov. 11, 2010 from: http://www.cosmeticdesign.com/news/ng.asp?id=60570-rainforest-brazil-active.

(Continued)

*Primary Examiner* — Qiuwen Mi

(74) *Attorney, Agent, or Firm* — Norton Rose Fulbright US LLP

(57) ABSTRACT

A method of treating skin is disclosed. The method can include topically applying to skin in need thereof, a composition comprising palmitoyl tetrapeptide 7, denatured alcohol, dimethicone, and squalane.

11 Claims, No Drawings

(56) References Cited

U.S. PATENT DOCUMENTS

| | | |
|---|---|---|
| 6,387,398 B1 | 5/2002 | Vollhardt et al. |
| 6,495,126 B1 | 12/2002 | Schiltz |
| 6,509,017 B1 | 1/2003 | Bergstrom et al. |
| 6,524,626 B2 | 2/2003 | Chen |
| 6,582,748 B1 | 6/2003 | Loh et al. |
| 6,610,838 B1 | 8/2003 | Bergstrom |
| 6,623,744 B2 | 9/2003 | Asmus et al. |
| 6,746,695 B1 | 6/2004 | Martin et al. |
| 6,814,970 B2 | 11/2004 | Sadziene et al. |
| 6,911,436 B2 | 6/2005 | Brown et al. |
| 6,974,799 B2 | 12/2005 | Lintner |
| 7,175,862 B2 | 2/2007 | Pusateri et al. |
| 7,182,935 B2 | 2/2007 | Ribeiro de Nazare et al. |
| 7,384,654 B2 | 6/2008 | Menon et al. |
| 7,384,656 B2 | 6/2008 | Menon et al. |
| 2002/0025303 A1 | 2/2002 | Fructus et al. |
| 2003/0007939 A1 | 1/2003 | Murad |
| 2003/0147977 A1 | 8/2003 | Goodman |
| 2003/0152544 A1 | 8/2003 | Chen |
| 2004/0109905 A1 | 6/2004 | Bagchi |
| 2004/0116511 A1 | 6/2004 | Malik |
| 2004/0120918 A1 | 6/2004 | Lintner et al. |
| 2004/0156818 A1 | 8/2004 | Lu et al. |
| 2004/0202726 A1 | 10/2004 | DeShay |
| 2005/0008667 A1 | 1/2005 | Liechty et al. |
| 2005/0025737 A1 | 2/2005 | Sebagh |
| 2005/0048143 A1 | 3/2005 | McAnalley et al. |
| 2005/0087452 A1 | 4/2005 | McAnalley et al. |
| 2005/0136141 A1 | 6/2005 | Stoner et al. |
| 2005/0163880 A1 | 7/2005 | Pusateri et al. |
| 2005/0169867 A1 | 8/2005 | Horino et al. |
| 2005/0196373 A1 | 9/2005 | Chen |
| 2005/0208564 A1 | 9/2005 | Ward et al. |
| 2005/0214413 A1 | 9/2005 | McAnalley et al. |
| 2005/0266018 A1 | 12/2005 | Boreyko et al. |
| 2006/0003353 A1 | 1/2006 | Ward et al. |
| 2006/0018868 A1 | 1/2006 | Dal Farra et al. |
| 2006/0045896 A1 | 3/2006 | Morariu |
| 2006/0083795 A1 | 4/2006 | Shatkina et al. |
| 2006/0093685 A1 | 5/2006 | Mower et al. |
| 2006/0188590 A1 | 8/2006 | Ono |
| 2006/0210609 A1 | 9/2006 | Mower |
| 2006/0210621 A1 | 9/2006 | Mower |
| 2006/0210688 A1 | 9/2006 | Mower |
| 2006/0210692 A1 | 9/2006 | Mower |
| 2006/0210697 A1 | 9/2006 | Mower |
| 2006/0211652 A1 | 9/2006 | Mower |
| 2006/0216251 A1 | 9/2006 | Morariu |
| 2006/0251750 A1 | 11/2006 | Tabor |
| 2006/0275511 A1 | 12/2006 | Murdock et al. |
| 2007/0003685 A1 | 1/2007 | Wantanabe |
| 2007/0020286 A1 | 1/2007 | Dattwyler et al. |
| 2007/0020358 A1 | 1/2007 | Mower |
| 2007/0031367 A1 | 2/2007 | Brown et al. |
| 2007/0065396 A1 | 3/2007 | Morariu |
| 2007/0086972 A1 | 4/2007 | Birnbaum |
| 2007/0087957 A1 | 4/2007 | Kidron |
| 2007/0116838 A1 | 5/2007 | Prakash et al. |
| 2007/0122364 A1 | 5/2007 | Kelly et al. |
| 2007/0141211 A1 | 6/2007 | Kolar et al. |
| 2007/0141223 A1 | 6/2007 | Moore et al. |
| 2007/0154439 A1 | 7/2007 | Dorf |
| 2007/0166275 A1 | 7/2007 | Gan et al. |
| 2007/0196298 A1 | 8/2007 | Kostick et al. |
| 2007/0202062 A1 | 8/2007 | Workman et al. |
| 2007/0202205 A1 | 8/2007 | Tsujita et al. |
| 2007/0207188 A1 | 9/2007 | Miller et al. |
| 2007/0237847 A1 | 10/2007 | Henry et al. |
| 2007/0243220 A1* | 10/2007 | Sandewicz ............... A61Q 1/08 424/401 |
| 2007/0248700 A1 | 10/2007 | Alberte et al. |
| 2007/0264401 A1 | 11/2007 | Taormina et al. |
| 2007/0269576 A1 | 11/2007 | Barton et al. |
| 2007/0275104 A1 | 11/2007 | Kornman et al. |
| 2007/0286908 A1 | 12/2007 | Clampitt |
| 2007/0292560 A1 | 12/2007 | Quan et al. |
| 2008/0004223 A1 | 1/2008 | Hlavka et al. |
| 2008/0044539 A1 | 2/2008 | Perlman et al. |
| 2008/0050331 A1 | 2/2008 | Giacomoni et al. |
| 2008/0050472 A1 | 2/2008 | Heuer et al. |
| 2008/0057157 A1 | 3/2008 | Almeida et al. |
| 2008/0076823 A1 | 3/2008 | Watkins et al. |
| 2008/0176305 A1 | 7/2008 | Sato et al. |
| 2008/0300529 A1 | 12/2008 | Reinstein |
| 2008/0305218 A1 | 12/2008 | Kahn |
| 2009/0028897 A1 | 1/2009 | Maestro et al. |
| 2009/0074822 A1 | 3/2009 | Declercq et al. |
| 2010/0215726 A1 | 8/2010 | Roth |

FOREIGN PATENT DOCUMENTS

| | | |
|---|---|---|
| AU | 2006237559 | 10/2006 |
| AU | 2007231781 | 10/2008 |
| AU | 2008100919 | 10/2008 |
| BR | 0107103 | 9/2003 |
| BR | 0203076 | 6/2004 |
| FR | 2 824 475 | 11/2002 |
| FR | 2 900 822 | 11/2007 |
| FR | 2 907 006 | 4/2008 |
| JP | H07-017824 | 8/1996 |
| JP | 11-246336 | 9/1999 |
| JP | 2000-327525 | 11/2000 |
| JP | 2000-327549 | 11/2000 |
| JP | 2000-327550 | 11/2000 |
| JP | 2000-327552 | 11/2000 |
| JP | 2001-031558 | 2/2001 |
| JP | 2001-031580 | 2/2001 |
| JP | 3431383 | 5/2003 |
| JP | 2005 306832 | 11/2005 |
| KR | 20000050304 | 8/2000 |
| KR | 20080071517 | 8/2008 |
| KR | 2008 094 457 | 10/2008 |
| KR | 20090011796 | 2/2009 |
| KR | 20090083082 | 8/2009 |
| WO | WO 1993/08306 | 4/1993 |
| WO | WO 1995/35379 | 12/1995 |
| WO | WO 1996/024327 | 8/1996 |
| WO | WO 1996/40718 | 12/1996 |
| WO | WO 2000/78966 | 12/2000 |
| WO | WO 2003/022070 | 3/2003 |
| WO | WO 2003/027258 | 4/2003 |
| WO | WO 2003/075869 | 9/2003 |
| WO | WO 2004/084833 | 10/2004 |
| WO | WO 2005/022116 | 3/2005 |
| WO | WO 2005/072537 | 8/2005 |
| WO | WO 2005/074959 | 8/2005 |
| WO | WO 2005/079741 | 9/2005 |
| WO | WO 2006/026713 | 3/2006 |
| WO | WO 2006/045112 | 4/2006 |
| WO | WO 2006/055550 | 5/2006 |
| WO | WO 2006/074278 | 7/2006 |
| WO | WO 2006/102108 | 9/2006 |
| WO | WO 2006/119408 | 11/2006 |
| WO | WO 2006/121985 | 11/2006 |
| WO | WO 2006/130939 | 12/2006 |
| WO | WO 2007/029238 | 3/2007 |
| WO | WO 2007/053096 | 5/2007 |
| WO | WO 2007/053097 | 5/2007 |
| WO | WO 2007/053098 | 5/2007 |
| WO | WO 2007/054789 | 5/2007 |
| WO | WO 2007/061900 | 5/2007 |
| WO | WO 2007/062206 | 5/2007 |
| WO | WO 2007/084752 | 7/2007 |
| WO | WO 2007/084754 | 7/2007 |
| WO | WO 2007/084998 | 7/2007 |
| WO | WO 2007/090393 | 8/2007 |
| WO | WO 2007/095261 | 8/2007 |
| WO | WO 2007/098205 | 8/2007 |
| WO | WO 2007/102913 | 9/2007 |
| WO | WO 2007/102915 | 9/2007 |
| WO | WO 2007/106473 | 9/2007 |
| WO | WO 2007/109600 | 9/2007 |
| WO | WO 2007/109884 | 10/2007 |
| WO | WO 2007/115382 | 10/2007 |

(56) References Cited

FOREIGN PATENT DOCUMENTS

| WO | WO 2007/131106 | 11/2007 |
|---|---|---|
| WO | WO 2007/133272 | 11/2007 |
| WO | WO 2007/133721 | 11/2007 |
| WO | WO 2007/137958 | 12/2007 |
| WO | WO 2007/140022 | 12/2007 |
| WO | WO 2008/008333 | 1/2008 |
| WO | WO 2008/009084 | 1/2008 |
| WO | WO 2008/018043 | 2/2008 |
| WO | WO 2008/028112 | 3/2008 |

OTHER PUBLICATIONS

"Berry good berry," *People*, Jan. 30, 2006.
"Cream Hair Colors," manufactured by Surya Nature, Apr. 2004.
"Daily Skin Shield Protective Moisture Lotion," manufactured by Unilever, Aug. 2006.
"Hair Mask," manufactured by Vedic Hindus, Jan. 2006.
"Kakadu Plum: Australian Patent Applications, Question 1172" The Senate Questions on Notice, Parliamentary Debates, Commonwealth of Australia, Mar. 10, 2009.
"Red Earth gains award," *The Sydney Morning Herald*, [Sydney] Oct. 22, 1997, Late Edition, Illawarra Mercury, p. 20.
"Shampoo for Color-Treated Hair," manufactured by Procter & Gamble, Jun. 2006.
Baran et al., *Textbook of Cosmetic Dermatology*, 3$^{rd}$ Edition, pp. 725-728, 2004.
Brand et al., "The nutritional composition of Australian Aboriginal bushfoods," *Food Technology in Australia*, 35:293-298, 1982.
Cao et al., "Oxygen-radical absorbance capacity assay for antioxidants," *Free Radic. Biol. Med.*, 14:303-311, 1993.
Coisson et al., "Euterpe oleracea juice as a functional pigment for yogurt," *Food Research International 38*, p. 893-897, 2005.
Correspondence from Dr. Daniel Robinson to Mary Kay Inc., dated Mar. 2009.
Correspondence from Dr. Daniel Robinson to the IP Australia Staff, dated Oct. 14, 2009.
CTFA International Cosmetic Ingredient Dictionary, Tenth edition, 2004.
Del Pozo-Insfran et al., "Phytochemical composition and pigment stability of Acai (Euterpe oleracea Mart.)," *J. Agric. Food Chem.*, 52:1539-1545, 2004.
Eurasian Office Action, issued in Eurasian Application No. 200801717, dated Jul. 1, 2009 (English Translation included).
Gorman et al., "An analysis of the use of plant products for commerce in remote Aboriginal communities of Northern Australia," *Economic Botany*, 60(4):362-373, 2006.
Hassimotto et al., "Antioxidant activity of dietary fruits, vegetables, and commercial frozen fruit pulps," *J. Agric. Good. Chem.* 53:2928-2935, 2005.
Jagetia et al., "Evaluation of the effect of ascorbic acid treatment on would healing in mice exposed to different doses of fractionated gamma radiation," *Radiat. Res.*, 159:371-80, 2003 (Abstract).
Kreuter, "Possibilities of using nanoparticles as carriers for drugs and vaccines," *J. Microencapsulation*, 5:115-127, 1988.
Lichtenthaler et al., "Total oxidant scavenging capacities of *Euterpe oleracea* Mart. (Acai) fruits," *Int. J. Food Sci. Nutr.*, 56:53-64, 2005.
McCutcheon's, Detergents and Emulsifiers, North American Edition, 1986.
Office Communication, issued in Australian Patent Application No. 2007205838, dated Oct. 21, 2009.
Office Communication, issued in Australian Patent Application No. 2007205838, dated Dec. 8, 2010.
Office Communication, issued in European Patent Application No. 07710236.6, dated Mar. 9, 2009.
Oram, "You're only as young as feel, so best start stocking up on miracle creams and potent anti-aging lotion says Trudy Oram," *The Advertiser*. [Adelaide, S. Australia] 1 State Edition, Jan. 18, 2005, p. 36.
Packman and Gams, "Topical moisturizers: quantification of their effect on superficial facial lines," *J. Soc. Cos. Chem.*, 29:70-90, 1978.
Palliardi, "Tried & Tested," *Sunday Herald Sun*, [Melbourne], First Edition, Sep. 8, 2002, p. Z.32.
PCT International Search Report and Written Opinion, issued in International Application No. PCT/US 07/60792, dated Oct. 2, 2007.
Remington's Pharmaceutical Sciences, 18th Ed. Mack Printing Company, 1289-1329, 1990.
Robinson, "Guest article: The biological patent predicament. Traditional knowledge and biological product derivative patents: Benefit-sharing and patent issues relating to Camu Camu, Kakadu Plum and Acai Plant Extracts," United Nations University, Institute of Advanced Studies, Traditional Knowledge Initiative, available online at http://www.unutki.org/news.php?doc_id=174, published online Apr. 30, 2010.
Schiltz et al. "Retinoic acid induces cyclic changes in epidermal thickness and dermal collagen and glycosaminoglycan biosynthesis rates," *J. Investigative Dermatology*, 87:663-667, 1986.
Stead, "Native magic," *The Sydney Morning Herald*, [Syndey] Mar. 14, 2000. Late Edition, Good Living, p. 20.
Taiwanese Search Report, issued in International Application No. 096102163, date of completion of search: Aug. 22, 2009 (English Translation).
Ward, "Beauty Spots," *The Sydney Morning Herald*, [Sydney] Jul. 21, 1997, Late Edition, Good Living, p. 8.
Woods, "A study of the intra-specific variations and commercial potential of *Terminalia ferdinandiana* exell (the Kakadu Plum)," M.S. Thesis. Northern Territory University, Darwin Jun. 1995.
Wynberg, "Rhetoric, Realism and Benefit Sharing: Use of Traditional Knowledge of *Hoodia* Species in the Development of an Appetite Suppressant," *Journal of World Intellectual Property*, 7(6):851-876, 2004.
International Search Report and Written Opinion issued in PCT/US2010/047164, dated Nov. 11, 2011.

\* cited by examiner

SKIN CARE FORMULATIONS

CROSS REFERENCE TO RELATED APPLICATIONS

This application is a continuation of U.S. application Ser. No. 15/798,944, filed Oct. 31, 2017, which is a continuation of U.S. application Ser. No. 14/482,053 (U.S. Pat. No. 9,833,642), filed Sep. 10, 2014, which is a continuation of U.S. application Ser. No. 14/223,729 filed Mar. 24, 2014 (U.S. Pat. No. 8,895,082), which is a continuation of U.S. application Ser. No. 13/237,573 (U.S. Pat. No. 8,691,300), filed Sep. 20, 2011, which is a continuation of U.S. application Ser. No. 12/871,557 (U.S. Pat. No. 8,048,456), filed Aug. 30, 2010, which claims the benefit of U.S. Provisional Application No. 61/238,001, filed Aug. 28, 2009. The contents of the referenced applications are incorporated into the present application by reference.

BACKGROUND OF THE INVENTION

A. Field of the Invention

The present invention relates generally to compositions that can be used to improve the skin's visual appearance. In one particular aspect, the composition includes a combination of palmitoyl tetrapeptide-7, methylsilanol mannuronate, *Lactobacillus* ferment, and plant extracts from *Punica granatum, Castanea sativa, Gossypium hirsutum*, and *Euterpe oleracea*. However, other skin active ingredients and formulations and combinations are contemplated throughout this specification.

B. Description of Related Art

With ageing, chronic exposure to adverse environmental factors, or malnutrition, the visual appearance, physical properties, and physiological functions of skin can change in ways that are considered visually undesirable. The most notable and obvious changes include the development of fine lines and wrinkles, loss of elasticity, increased sagging, loss of firmness, loss of color evenness or tone, coarse surface texture, and mottled pigmentation. Less obvious, but measurable changes which occur as skin ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's ability to remodel and repair itself. Many of the alterations in appearance and function of the skin are caused by changes in the outer epidermal layer of the skin, while others are caused by changes in the lower dermis.

One problem associated with existing skin care products is that they tend to focus on a particular skin condition without consideration of other skin conditions. This results in a user having to purchase several different products and apply several different products throughout the day to obtain the desired results. Further, the majority of such products are designed to be used throughout the daytime, which is a period of time that the skin is actively beings assaulted with caustic environmental factors such as UV light, pollution, chemicals, smoke, etc. Therefore, the skin may not be completely receptive to the benefits that a skin composition can provide.

SUMMARY OF THE INVENTION

While the compositions of the present invention have the ability to treat skin during the daytime, the inventors discovered that a unique combination of skin active ingredients (e.g., palmitoyl tetrapeptide-7, methylsilanol mannuronate, *Lactobacillus* ferment, and plant extracts from *Punica granatum, Castanea sativa, Gossypium hirsutum*, and *Euterpe oleracea*) works surprisingly well in treating skin during the evening hours. This combination of ingredients is designed to work in sync with a person's skin rhythms to help the skin recover/recuperate during sleep mode.

In one aspect, there is disclosed a method of treating skin during sleep. The method can include topically applying a composition to a user's skin prior to the user falling asleep. The composition can include a chemically compatible combination of skin active ingredients comprising palmitoyl tetrapeptide-7, methylsilanol mannuronate, and *Lactobacillus* ferment, and a chemically compatible combination of skin active ingredients comprising plant extracts from *Punica granatum, Castanea sativa, Gossypium hirsutum*, and *Euterpe oleracea*, and a dermatologically acceptable vehicle, a vehicle which can have hydrating and/or moisturization properties. The method can further include removing the composition from the user's skin after the user wakes up. This can result in rejuvenation or replenishing the skin during the evening hours by using the unique combination of ingredients. This combination is proven to be chemically compatible (i.e., they are able to coexist together without detrimentally affecting their individual skin efficacy abilities) and skin friendly in that the combination does not appear to irritate the skin. The result of this combination is a superior way to rejuvenate the skin during the evening hours, which ultimately provides for an effective way to treat a wide variety of skin conditions such as firming/toning the skin, increasing the skin's elasticity, reducing the appearance of dark spots or aged spots, evening out the skin's tone, reducing the appearance of fine lines and wrinkles, reducing other signs of premature skin aging, and reducing the appearance of expression lines. The evening hours typically includes the time the sun goes down to the time the sun comes up. The composition can be applied during the evening hours prior to falling asleep and can be removed when the user awakens. The composition can be applied to all types of skin such as the face, neck, decolette, arms, hands, body, legs, feet, etc. The composition can be formulated as a cream, lotion, gel, gel-like cream, serum, etc. The color of the composition can be opaque, transparent, translucent, etc. The composition can be formulated for use on dry skin, normal skin, oily skin, combination skin, etc. The dermatologically acceptable vehicle can be formulated to moisturize skin, hydrate skin, to provide a substantive effect in that the composition has the ability to remain on the skin even during sleep mode. In one aspect, the dermatologically acceptable vehicle comprises at least 50% by weight of water, 3 to 10% by weight of glycerin, 3 to 10% by weight of butylene glycol, 1 to 3% by weight of glyceryl stearate, 1 to 5% by weight of caprylic/capric triglyceride, and 1 to 5% by weight of hydrogenated polydecene. In another aspect, the dermatologically acceptable vehicle comprises water, glycerin, butylene glycol, glyceryl stearate, caprylic/capric triglyceride, and hydrogenated polydecene. The ratio of water to glycerin can be important for skin types. In some instances, the water:glycerine ratio is about 5:1 to about 20:1 (or 6:1, 7:1, 8:1, 9:1, 10:1, 11:1, 12:1, 13:1, 14:1, 15:1, 16:1, 17:1, 18:1, 19:1 or any range therein) based on the total weight of the composition. The composition may not have a sunscreen agent, a cyclomethicone, an alpha hydroxy acid, a beta hydroxy acid, an oil, an acid or base based molecule, a vitamin, and/or any other skin active ingredients or other skin active ingredients in skin active amounts.

Also disclosed in a topical skin care composition comprising a chemically compatible combination of skin active ingredients comprising palmitoyl tetrapeptide-7, methylsilanol mannuronate, and *Lactobacillus* ferment, a chemically compatible combination of skin active ingredients comprising plant extracts from *Punica granatum, Castanea sativa, Gossypium hirsutum*, and *Euterpe oleracea*, and a dermatologically acceptable vehicle. The dermatologically acceptable vehicle can include at least 50% by weight of water, 3 to 10% by weight of glycerin, 3 to 10% by weight of butylene glycol, 1 to 3% by weight of glyceryl stearate, 1 to 5% by weight of caprylic/capric triglyceride, and 1 to 5% by weight of hydrogenated polydecene. The dermatologically acceptable vehicle can include water, glycerin, butylene glycol, glyceryl stearate, caprylic/capric triglyceride, and hydrogenated polydecene. In certain instances, the water: glycerine ratio is about 5:1 to about 20:1 (or 6:1, 7:1, 8:1, 9:1, 10:1, 11:1, 12:1, 13:1, 14:1, 15:1, 16:1, 17:1, 18:1, 19:1 or any range therein) based on the total weight of the composition. In further aspects, the dermatologically acceptable vehicle can include water, glycerin, a combination of butylene glycol and propylene glycol, glyceryl stearate, dimethicone, disodium EDTA, steareth-20, polyethylene glycol-40 stearate, caprylic/capric triglyceride, hydrogenated polydecene, methyl trimethicone, butyrospermum parkii, sodium polyacrylate, and butylated hydroxytolene. The composition can be an emulsion, a gel, a cream, a lotion, a serum, etc. The composition can be translucent, transparent, or opaque. The composition can be formulated for normal, dry, oily, or combination skin-types. The composition may not have a sunscreen agent, a cyclomethicone, an alpha hydroxy acid, a beta hydroxy acid, an oil, an acid or base based molecule, a vitamin, and/or any other skin active ingredients or other skin active ingredients in skin active amounts.

In still another aspect, there is disclosed a combination of palmitoyl tetrapeptide-7, methylsilanol mannuronate, *Lactobacillus* ferment, and plant extracts from *Punica granatum, Castanea sativa, Gossypium hirsutum*, and *Euterpe oleracea*. The combination can be in an aqueous solution, a hydrophobic solution, an alcohol solution, a glycolic solution, in powdered form, etc. The combination can be placed in compositions for skin, food, medicines, pharmaceuticals, injectibles, etc.

In one embodiment, there is disclosed a method of firming skin or reducing the appearance of fine lines or wrinkles comprising topically applying any one of the compositions of the present invention to skin in need of such treatment. The composition can include a chemically compatible combination of skin active ingredients comprising palmitoyl tetrapeptide-7, methylsilanol mannuronate, and *Lactobacillus* ferment, a chemically compatible combination of skin active ingredients comprising plant extracts from *Punica granatum, Castanea sativa, Gossypium hirsutum*, and *Euterpe oleracea*, and a dermatologically acceptable vehicle. The composition can be applied to fine lines or wrinkles, sagging skin, skin areas prone to sagging, etc.

In an alternative embodiment of the present invention there is disclosed compositions of the present invention can include Hydrolyzed *Myrtus communis* (myrtle) leaf extract, *Cucurbita pepo* (pumpkin) seed extract, *Gossypium hirsutum* (cotton) extract, *Castanea sativa* (chestnut) seed extract, *Euterpe oleracea* (acai) fruit extract, *Punica granatum* (pomegranate) sterols or fruit extract, *Terminalia ferdinandiana* (kakadu plum) fruit extract, *Ferula foetida* (ferula) root extract, *Myriciaria Dubia* (camu camu) fruit extract, Palmitoyl tetrapeptide-3, Monomethylsilanetriol mannuronate, *Lactobacillus* ferment extract, or *Alteromonas* ferment extract, or combinations thereof. In one instance, the combination includes palmitoyl tetrapeptide-7, methylsilanol mannuronate, *Lactobacillus* ferment, and plant extracts from *Punica granatum, Castanea sativa, Gossypium hirsutum*, and *Euterpe oleracea*. Additional ingredients such as *Helianthus annus* (sunflower) seed extract, dipotassium glycyrrhizate, ascorbyl glucoside, *Argania spinosa* (argan) seed kernel extract, *Secale cereale* (rye) seed extract, *Linum usitatissimum* (linseed) seed extract, *Malpighia punicifolia* (acerola) fruit extract, *Pinus sylvestris* bark extract, *Ribes nigrum* (black currant) leaf extract, palmitoyl oligopeptide, palmitoyl tetrapeptide-7, or adenosine, or any combination thereof, can also be incorporated into the compositions of the present invention. Further, as shown in the figures and examples (which are incorporated into this section by reference), the inventors have discovered that the combination of any one of Hydrolyzed *Myrtus communis* (myrtle) leaf extract, *Cucurbita pepo* (pumpkin) seed extract, *Gossypium hirsutum* (cotton) extract, *Castanea sativa* (chestnut) seed extract, *Euterpe oleracea* (acai) fruit extract, *Punica granatum* (pomegranate) sterols or fruit extract, *Terminalia ferdinandiana* (kakadu plum) fruit extract, *Ferula foetida* (ferula) root extract, *Myriciaria Dubia* (camu camu) fruit extract, Palmitoyl tetrapeptide-3, Monomethylsilanetriol mannuronate, *Lactobacillus* ferment extract, or *Alteromonas* ferment extract, or combinations thereof, produce synergistic and complimentary effects that are beneficial to skin.

In certain embodiments, the compositions are formulated into topical skin care compositions. The compositions can be cosmetic compositions. In other aspects, the compositions can be included in a cosmetic vehicle. Non-limiting examples of cosmetic vehicles are disclosed in other sections of this specification and are known to those of skill in the art. Examples of cosmetic vehicles include emulsions (e.g., oil-in-water and water-in-oil emulsions), creams, lotions, solutions (e.g., aqueous or hydro-alcoholic solutions), anhydrous bases (e.g., lipstick or a powder), gels, and ointments. In other non-limiting embodiments, the compositions of the present invention can be included in anti-aging, cleansing, or moisturizing products. The compositions can also be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result (e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc., as measured on a Brookfield Viscometer using a TC spindle at 2.5 rpm at 25° C.).

The compositions in non-limiting aspects can have a pH of about 6 to about 9. In other aspects, the pH can be 1, 2, 3, 4, 5, 6, 7, 8, 9, 10, 11, 12, 13, or 14. Compositions of the present invention can have UVA and UVB absorption properties. The compositions can have an sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

The compositions of the present invention can also be modified to have a desired oxygen radical absorbance capacity (ORAC) value. In certain non-limiting aspects, the compositions of the present invention can be modified to have an ORAC value per mg of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 95, 100, 200, 300, 400, 500, 600, 700, 800, 900, 1000, 2000, 3000, 4000, 5000, 6000, 7000, 8000, 9000, 10000, 15000, 20000, 30000, 50000, 100000 or more or any range derivable therein.

In particular aspects, the compositions can be oil-free, substantially anhydrous, and/or anhydrous. Other aspects include compositions having water.

In one aspect of the present invention, there is disclosed a topical skin care composition that include a skin active ingredient selected from the group consisting of: Hydrolyzed *Myrtus communis* (myrtle) leaf extract; *Cucurbita pepo* (pumpkin) seed extract; *Gossypium hirsutum* (cotton) extract; *Castanea sativa* (chestnut) seed extract; *Euterpe oleracea* (acai) fruit extract; *Punica granatum* (pomegranate) sterols or fruit extract; *Terminalia ferdinandiana* (kakadu plum) fruit extract; *Ferula foetida* (ferula) root extract; *Myriciaria Dubia* (camu camu) fruit extract; Palmitoyl tetrapeptide-3; Monomethylsilanetriol mannuronate; *Lactobacillus* ferment extract; and *Alteromonas* ferment extract; and any combination of such skin active ingredients. In one instance, the combination includes palmitoyl tetrapeptide-7, methylsilanol mannuronate, *Lactobacillus* ferment, and plant extracts from *Punica granatum, Castanea sativa, Gossypium hirsutum*, and *Euterpe oleracea*. In certain aspects, the compositions can include all of these skin active ingredients. The compositions of the present invention can also include any one of, any combination of, or all of the following additional ingredients: water, a chelating agent, a moisturizing agent, a preservative, a thickening agent, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

In another embodiment, there is disclosed a topical skin care composition comprising: palmitoyl tetrapeptide 7; *Euterpe oleracea* (acai) fruit extract or *Terminalia ferdinandiana* (kakadu plum) fruit extract or a combination thereof; and a dermatologically acceptable vehicle comprising any one of or all of the following: water; glycerin; butylene glycol; propylene glycol; and disodium EDTA, wherein the topical skin care composition is formulated for topical application to skin. In particular aspects, the composition includes any one of or all of the following: 30 to 80% by weight of water; 3 to 25% by weight of glycerin; 0.01 to 5% by weight of butylene glycol; 0.1 to 1% by weight of propylene glycol; and 0.01 to 0.5% by weight of disodium EDTA. In other aspects, the ratio of water to glycerin can be from about 0.5:1 to about 20:1 or anything in between (e.g., 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, or 19:1, or any range therein) based on the total weight of the composition. In certain aspects, the range can be from about 6:1 to about 20:1, whereas in other aspects it can be about 0.5:1 to about 2:1. In other aspects, the ratio of propylene glycol to disodium EDTA in the composition can be from about 1:1 to about 30:1 or anything in between (e.g., 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1 or any range therein) based on the total weight of the composition. In particular embodiments, the ratio of propylene glycol to disodium EDTA can be from about 1.5:1 to about 3.5:1 based on the total weight of the composition or from about 15:1 to about 30:1 based on the total weight of the composition. The composition can further include any one of or all of the following: phenoxyethanol; steareth-20; chlorhexidine diglunonate; potassium sorbate; and a preservative selected from the group consisting of methyparaben, propylparaben, butylparaben, ethylparaben, and isobutylparaben, and any combination thereof. In certain aspects, the composition can include any one of or all of the following: 0.00001 to 1% by weight of phenoxyethanol; 0.0001 to 0.1% by weight of steareth-20; 0.00001 to 0.1% by weight of chlorhexidine diglunonate; 0.000001 to 0.01% by weight of potassium sorbate; and 0.000001 to 1% by weight of a preservative selected from the group consisting of methyparaben, propylparaben, butylparaben, ethylparaben, and isobutylparaben, and any combination thereof. In certain aspects, the composition can further include any one of or all of the following skin active ingredients: Hydrolyzed *Myrtus communis* (myrtle) leaf extract; *Cucurbita pepo* (pumpkin) seed extract; *Gossypium hirsutum* (cotton) extract; *Castanea sativa* (chestnut) seed extract; *Punica granatum* (pomegranate) sterols or fruit extract; *Ferula foetida* (ferula) root extract; *Myriciaria Dubia* (camu camu) fruit extract; methylsilanol mannuronate; *Lactobacillus* ferment extract; or *Alteromonas* ferment extract; or any combination thereof. The amount of any one of the aforementioned ingredients within a given composition can vary to as little as 0.0000001% to 99.9% or any range or integer divisible therein as discussed in other sections of the specification, which are incorporated by reference.

In particular aspects of the present invention, there is disclosed a topical skin care composition that includes any one of, any combination of, or all of the following ingredients: palmitoyl tetrapeptide 7; *Euterpe oleracea* (acai) fruit extract or *Terminalia ferdinandiana* (kakadu plum) fruit extract or a combination thereof; water; glycerin; butylene glycol; propylene glycol; disodium EDTA; phenoxyethanol; steareth-20; chlorhexidine diglunonate; potassium sorbate; a preservative; *Cucurbita pepo* (pumpkin) seed extract; Lactobaccillus ferment extract; *Myriciaria Dubia* (camu camu) fruit extract; Hydrolyzed *Myrtus communis* (myrtle) leaf extract; *Alteromonas* ferment extract; or *Ferula foetida* (ferula) root extract. The composition can include 40 to 50% by weight of water, 3 to 5% by weight of glycerin, and 2 to 5% by weight of butylene glycol. The composition can further include any one of, any combination of, or all of the following: denatured alcohol; behenyl alcohol; nylon-12; ethylene/acrylic acid copolymer; glyceryl stearate; or aluminum starch octenylsuccinate. The amounts of such ingredients can be 2 to 5% by weight of denatured alcohol; 1 to 3% by weight of behenyl alcohol; 1 to 3% by weight of nylon-12; 1 to 3% by weight of ethylene/acrylic acid copolymer; 0.1 to 2% by weight of glyceryl stearate; or 0.1 to 2% by weight of aluminum starch octenylsuccinate. The composition can further include a UV absorbing agent selected from the group consisting of homosalate, octisalate, oxybenzone, and avobenzone, and any combination thereof.

In still another embodiment, there is disclosed a topical skin care composition that includes any one of, any combination of, or all of the following ingredients: palmitoyl tetrapeptide 7; *Euterpe oleracea* (acai) fruit extract or *Terminalia ferdinandiana* (kakadu plum) fruit extract or a combination thereof; water; glycerin; butylene glycol; propylene glycol; disodium EDTA; phenoxyethanol; steareth-20; chlorhexidine diglunonate; potassium sorbate; a preservative; *Cucurbita pepo* (pumpkin) seed extract; Lactobaccillus ferment extract; *Myriciaria Dubia* (camu camu) fruit extract; Hydrolyzed *Myrtus communis* (myrtle) leaf extract; *Alteromonas* ferment extract; or *Ferula foetida* (ferula) root extract. The composition can include 40 to 50% by weight of water, 3 to 5% by weight of glycerin, and 2 to 5% by weight of butylene glycol. The composition can further include any one of, any combination of, or all of the following: denatured alcohol; behenyl alcohol; ethylene/acrylic acid copolymer; glyceryl stearate; or aluminum starch octenylsuccinate. The amount of such ingredients can be 2 to 5% by weight of denatured alcohol; 1 to 3% by weight of behenyl alcohol; 1 to 3% by weight of ethylene/acrylic acid copolymer; 0.1 to 2% by weight of glyceryl stearate; and 0.1 to 2% by weight of aluminum starch octenylsuccinate. The composition can further include a UV absorbing agent selected from the group consisting of homosalate, octisalate, oxybenzone, and avobenzone, and any combination thereof. The composition can be formulated as an oil-in-water emulsion.

In even another aspect, there is disclosed a topical skin care composition that includes any one of, any combination of, or all of the following ingredients: palmitoyl tetrapeptide 7; *Euterpe oleracea* (acai) fruit extract or *Terminalia ferdinandiana* (kakadu plum) fruit extract or a combination thereof; water; glycerin; butylene glycol; propylene glycol; disodium EDTA; phenoxyethanol; steareth-20; chlorhexidine diglunonate; potassium sorbate; a preservative; *Myriciaria Dubia* (camu camu) fruit extract; or Hydrolyzed *Myrtus communis* (myrtle) leaf extract. The topical skin care composition can include 35 to 45% by weight of water and 20 to 30% by weight of glycerin. The composition can further include any one of, any combination of, or all of the following additional ingredients: potassium myristate; cocamidopropyl betaine; myristic acid; potassium laurate; sodium myristoyl glutamate; PEG-32; sorbitol; or glyceryl stearate. The composition can include 5 to 10% by weight of potassium myristate; 3 to 7% by weight of cocamidopropyl betaine; 2 to 5% by weight of myristic acid; 2 to 5% by weight of potassium laurate; 2 to 5% by weight of sodium myristoyl glutamate; 1 to 3% by weight of PEG-32; 1 to 3% by weight of sorbitol; and 1 to 3% by weight of glyceryl stearate.

In still another embodiment, there is disclosed a topical skin care composition that includes any one of, any combination of, or all of the following ingredients: palmitoyl tetrapeptide 7; *Euterpe oleracea* (acai) fruit extract or *Terminalia ferdinandiana* (kakadu plum) fruit extract or a combination thereof; water; glycerin; butylene glycol; propylene glycol; disodium EDTA; phenoxyethanol; steareth-20; chlorhexidine diglunonate; potassium sorbate; a preservative; *Myriciaria Dubia* (camu camu) fruit extract; or Hydrolyzed *Myrtus communis* (myrtle) leaf extract. The topical skin care composition can include 30 to 40% by weight of water and 35 to 45% by weight of glycerin. The topical skin care composition can further include any one of, any combination of, or all of the following: potassium myristate; potassium laurate; myristic acid; stearic acid; sodium chloride; potassium stearate; PEG-40 stearate; sodium methyl cocoyl taurate; lauric acid; glycol stearate; or sodium cocyl glycinate. The composition can include 3 to 7% by weight of potassium myristate; 2 to 5% by weight of potassium laurate; 0.5 to 2% by weight of myristic acid; 1 to 3% by weight of stearic acid; 0.5 to 2% by weight of sodium chloride; 2 to 5% by weight of potassium stearate; 1 to 5% by weight of PEG-40 stearate; 1 to 3% by weight of sodium methyl cocoyl taurate; 0.5 to 2% by weight of lauric acid; 0.5 to 2% by weight of glycol stearate; and 0.5 to 2% by weight of sodium cocyl glycinate.

In yet another embodiment, there is disclosed a topical skin care composition that includes any one of, any combination of, or all of the following ingredients: palmitoyl tetrapeptide 7; *Euterpe oleracea* (acai) fruit extract or *Terminalia ferdinandiana* (kakadu plum) fruit extract or a combination thereof; water; glycerin; butylene glycol; propylene glycol; disodium EDTA; phenoxyethanol; steareth-20; chlorhexidine diglunonate; potassium sorbate; a preservative; *Punica granatum* (pomegranate) sterols or fruit extract; *Castanea sativa* (chestnut) seed extract; *Gossypium hirsutum* (cotton) extract; or methylsilanol mannuronate. The composition can include 65 to 75% by weight of water, 3 to 5% by weight of glycerin, and 7 to 12% by weight of butylene glycol. The composition can further include any one of, any combination of, or all of the following: glyceryl stearate; caprylic/capric triglyceride; or hydrogenated polydecene. The composition can include 0.5 to 2% by weight glyceryl stearate; 3 to 7% by weight of caprylic/capric triglyceride; and 1 to 3% by weight of hydrogenated polydecene. The topical skin care composition can be formulated as a water-in-oil emulsion.

In another embodiment, there is disclosed a topical skin care composition that includes any one of, any combination of, or all of the following ingredients: palmitoyl tetrapeptide 7; *Euterpe oleracea* (acai) fruit extract or *Terminalia ferdinandiana* (kakadu plum) fruit extract or a combination thereof; water; glycerin; butylene glycol; propylene glycol; disodium EDTA; phenoxyethanol; steareth-20; chlorhexidine diglunonate; potassium sorbate; a preservative; *Lactobacillus* ferment extract; *Punica granatum* (pomegranate) sterols or fruit extract; *Castanea sativa* (chestnut) seed extract; *Gossypium hirsutum* (cotton) extract; or methylsilanol mannuronate. The composition can include 55 to 65% by weight of water, 5 to 10% by weight of glycerin, and 2 to 5% by weight of butylene glycol. The composition can further include any one of, any combination of, or all of the following: glyceryl stearate; dimethicone; PEG-40 stearate; caprylic/capric triglyceride; hydrogenated polydecene; methyl trimethicone; shea butter; a biosaccharide gum; or octyldodecyl myristate. The composition can include 0.5 to 2% by weight of glyceryl stearate; 2 to 5% by weight of dimethicone; 0.5 to 2% by weight of PEG-40 stearate; 2 to 5% by weight of caprylic/capric triglyceride; 3 to 7% by weight of hydrogenated polydecene; 2 to 5% by weight of methyl trimethicone; 2 to 5% by weight of shea butter; 1 to 5% by weight of a biosaccharide gum; and 1 to 3% by weight of octyldodecyl myristate. The composition can be formulated as a water-in-oil emulsion.

In a particular embodiment, there is disclosed an oil-in-water emulsion comprising any one of, any combination of, or all of the following ingredients: water; glycerin; butylene glycol; sodium polyacrylate; disodium EDTA; caprylic/capric triglyceride; cyclomethicone; glyceryl stearate; dimethicone; cetearyl alcohol; C12-22 alcohols; c12-20 alkyl glucoside; a preservative, and skin active ingredient. The amount of such ingredients can vary as disclosed throughout this specification. Non-limiting ranges of the amounts of such ingredients in a formulation (either by weight or volume) include: water (q.s. to 100%); glycerin (3% to 5%); butylene glycol (5% to 10%); sodium polyacrylate (0.1% to 1%); disodium EDTA (0.01% to 1%); caprylic/capric triglyceride (1% to 7%); cyclomethicone (0.01% to 3%); glyceryl stearate (0.5% to 3%); dimethicone (0.1% to 2%); cetearyl alcohol (0.1% to 2%); C12-22 alcohols (0.1% to 3%); C12-20 alkyl glucoside (0.01% to 1%); a preservative (0.01% to 5%), and skin active ingredient (0.001% to 5%). Additional ingredients can also be included, non-limiting examples of which include: 2 to 5% by weight of denatured alcohol; 1 to 3% by weight of behenyl alcohol; 1 to 3% by weight of nylon-12; 1 to 3% by weight of ethylene/acrylic acid copolymer; 0.1 to 2% by weight of glyceryl stearate; 0.1 to 2% by weight of aluminum starch octenylsuccinate; and/or a combination of *Cucurbita pepo* (pumpkin) seed extract, Lactobaccillus ferment extract, *Terminalia ferdinandiana* (kakadu plum) fruit extract, *Myriciaria Dubia* (camu camu) fruit extract, Hydrolyzed *Myrtus communis* (myrtle) leaf extract, *Alteromonas* ferment extract, and/or *Ferula foetida* (ferula) root extract; or any combination thereof.

In another particular embodiment, there is disclosed an oil-in-water emulsion comprising any one of, any combination of, or all of the following ingredients: water; glycerin; butylene glycol; disodium EDTA; acrylates copolymer; polyacrylamide; glyceryl stearate and PEG-100 stearate; cetyl alcohol; C13-14 isoparaffin; laureth-7; cetearyl alcohol; ceteth-20 phosphate; dicetyl phosphate; homosalate; dimethicone; octisalate; oxybenzone; avobenzone; preservative; skin actives; and additional ingredients. Non-limiting ranges of the amounts of such ingredients in a formulation (either by weight or volume) include: water (q.s. to 100%); glycerin (3% to 5%); butylene glycol (1% to 3%); disodium EDTA (0.01% to 1%); acrylates copolymer (1% to 3%); polyacrylamide (0.01% to 1%); glyceryl stearate and PEG-100 stearate (1% to 3%); cetyl alcohol (1% to 3%); C13-14 isoparaffin (0.01% to 1%); laureth-7 (0.01% to 1%); cetearyl alcohol (0.01% to 1%); ceteth-20 phosphate (0.1% to 1%); dicetyl phosphate (0.01% to 1%); homosalate (5% to 15%); dimethicone (0.01% to 1%); octisalate (3% to 8%); oxybenzone (3% to 8%); avobenzone (1% to 5%); preservative (0.01% to 5%); and skin actives (0.01% to 5%). Additional ingredients can also be included, non-limiting examples of which include: 2 to 5% by weight of denatured alcohol; 1 to 3% by weight of behenyl alcohol; 1 to 3% by weight of ethylene/acrylic acid copolymer; 0.1 to 2% by weight of glyceryl stearate; 0.1 to 2% by weight of aluminum starch octenylsuccinate; and/or a combination of *Cucurbita pepo* (pumpkin) seed extract, Lactobaccillus ferment extract, *Terminalia ferdinandiana* (kakadu plum) fruit extract, *Myriciaria Dubia* (camu camu) fruit extract, Hydrolyzed *Myrtus communis* (myrtle) leaf extract, *Alteromonas* ferment extract, and/or *Ferula foetida* (ferula) root extract; or any combination thereof.

In still another particular embodiment, there is disclosed a cleanser comprising any one of, any combination of, or all of the following ingredients: water; glycerin; cocamidopropyl betaine; potassium myristate; stearic acid; disodium EDTA; triethanolamine; preservatives; skin active ingredients; and additional ingredients. Non-limiting ranges of the amounts of such ingredients in a formulation (either by weight or volume) include: water (q.s. to 100%); glycerin (20% to 30%); cocamidopropyl betaine (10% to 20%); potassium myristate (5% to 10%); stearic acid (1% to 3%); disodium EDTA (0.01% to 1%); triethanolamine (0.01% to 1%); preservative (0.01% to 5%); and skin actives (0.01% to 5%). Additional ingredients can also be included, non-limiting examples of which include: 2 to 5% by weight of potassium laurate; 2 to 5% by weight of myristic acid; 2 to 5% by weight of sodium myristoyl glutamate; 1 to 3% by weight of PEG-32; 1 to 3% by weight of sorbitol; 1 to 3% by weight of glyceryl stearate; and/or a combination of *Terminalia ferdinandiana* (kakadu plum) fruit extract, *Myriciaria Dubia* (camu camu) fruit extract, and/or Hydrolyzed *Myrtus communis* (myrtle) leaf extract; or any combination thereof.

Also disclosed is a method of treating or preventing a skin condition comprising topically applying any composition disclosed throughout the specification and claims to skin having a skin condition or at risk of having a skin condition, wherein topical application of the composition to the skin condition treats the skin condition or prevents the skin condition from forming. In particular embodiments, the skin condition is a fine line or wrinkle, dry or flaky skin, erythema, sensitive skin, or inflamed skin. In particular aspects, erythema, sensitive skin, or inflamed skin is caused by skin sunburn, electrical treatments of skin, skin burns, contact allergies, systemic allergies, skin toxicity, exercise, insect stings, bacterial infection, viral infection, fungal infection, protozoa infection, massage, or windburn. In other aspects, the following additional skin conditions can be treated or prevented in accordance with the methods and compositions disclosed throughout the specification and claims: pruritus, spider veins, lentigo, age spots, senile purpura, keratosis, melasma, blotches, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, and other inflammatory skin conditions. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). The method can further comprise identifying a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein. The method can also include topically applying an amount effective to: increase the stratum corneum turnover rate of the skin; increase collagen synthesis in fibroblasts; increase cellular anti-oxidant defense mechanisms (e.g., exogenous additions of anti-oxidants can bolster, replenish, or prevent the loss of cellular antioxidants such as catalase and glutathione in skin cells (e.g., keratinocytes, melanocytes, langerhans cells, etc.) which will reduce or prevent oxidative damage to the skin, cellular, proteins, and lipids); inhibit melanin production in melanocytes; reduce or prevent oxidative damage to skin (including reducing the amount lipid peroxides and/or protein oxidation in the skin). In one instance, the composition includes palmitoyl tetrapeptide-7, methylsilanol mannuronate, *Lactobacillus* ferment, and plant extracts from *Punica granatum, Castanea sativa, Gossypium hirsutum*, and *Euterpe oleracea*, which can treat a wide range of skin conditions.

Also disclosed is a method of reducing the appearance of uneven skin tone comprising topically applying any one of the compositions disclosed throughout the specification and claims to skin having an uneven skin tone, wherein topical application of the composition to uneven skin tone reduces the appearance of uneven skin tone. In one instance, the composition includes palmitoyl tetrapeptide-7, methylsilanol mannuronate, *Lactobacillus* ferment, and plant extracts from *Punica granatum, Castanea sativa, Gossypium hirsutum*, and *Euterpe oleracea*.

In another embodiment, there is disclosed a method of reducing pain associated with erythema, sensitive skin, or inflamed skin, comprising topically applying any one of the compositions disclosed throughout the specification and claims to erythemic, sensitive, or inflamed skin, wherein topical application of the composition to erythemic, sensitive, or inflamed skin reduces the pain associated with erythema, sensitive skin, or inflamed skin. In one instance, the composition includes palmitoyl tetrapeptide-7, methylsilanol mannuronate, *Lactobacillus* ferment, and plant extracts from *Punica granatum, Castanea sativa, Gossypium hirsutum*, and *Euterpe oleracea*.

In still another aspect, there is disclosed a method of reducing the appearance of symptoms associated with erythema, sensitive skin, or inflamed skin, comprising topically applying any one of the compositions disclosed throughout the specification and claims erythemic, sensitive, or inflamed skin, wherein topical application of the composition to erythemic, sensitive, or inflamed skin reduces the appearance of symptoms associated with erythema, sensitive skin, or inflamed skin. In one instance, the composition includes palmitoyl tetrapeptide-7, methylsilanol mannuronate, *Lactobacillus* ferment, and plant extracts from *Punica granatum, Castanea sativa, Gossypium hirsutum*, and *Euterpe oleracea*.

Also disclosed is a method of removing dirt, oil, or make-up from skin comprising: applying any one of the compositions disclosed throughout the specification and claims to skin in need of removal of dirt, oil, or make-up; and removing the composition from the skin with water within about 1, 2, 3, 4, 5, 6, 7, 8, 9, 10, 11, 12, 13, 14, 15, 20, 30, 40, 50, 60, 120, 180, or minutes after application, wherein dirt, oil, or makeup is removed from the skin. In particular aspects, the composition is applied to dirt on the skin, and wherein the dirt is removed from the skin. In other aspects, the composition is applied to oil on the skin, and wherein the oil is removed from the skin. In another embodiment, the composition is applied to make-up on the skin, and wherein the make-up is removed from the skin.

In other aspect, there is disclosed a method of increasing collagen production in a skin cell comprising topically applying any one of the compositions disclosed throughout the specification and claims to a skin cell in need of collagen production, wherein the topical application of the composition to the skin cell increases collagen production in the skin cell. Non-limiting examples of such cells include human epidermal keratinocyte, human fibroblast dermal cell, human melanocytes, three dimensional human cell-derived in vitro tissue equivalents comprising human keratinocytes, human fibroblasts, or human melanocytes, or any combination thereof (e.g., combination of human keratinocytes and human fibroblasts or a combination of human keratinocytes and human melanocytes). In one instance, the composition includes palmitoyl tetrapeptide-7, methylsilanol mannuronate, *Lactobacillus* ferment, and plant extracts from *Punica granatum, Castanea sativa, Gossypium hirsutum*, and *Euterpe oleracea*.

Also disclosed is a method of lightening skin or evening skin tone comprising applying any one of the compositions disclosed throughout the specification and claims to skin. The method can further comprise identify a person in need of lightening skin or evening skin tone. The methods can further include inhibiting melanogenesis in a skin cell, inhibiting tyrosinase or tyrosinase synthesis in a skin cell, or inhibiting melanin transport to keratinocytes in a skin cell. The composition can act as an alpha melanin stimulatory hormone antagonist. The composition can even out pigmentation of the skin. In non-limiting aspect, lightening skin can include reducing the appearance of an age spot, a skin discoloration, or a freckle by topical application of the composition to skin having an age spot, skin discoloration, a freckle, etc. In one instance, the composition includes palmitoyl tetrapeptide-7, methylsilanol mannuronate, *Lactobacillus* ferment, and plant extracts from *Punica granatum, Castanea sativa, Gossypium hirsutum*, and *Euterpe oleracea*.

Also disclosed is a method of treating hyperpigmentation comprising applying any one of the compositions disclosed throughout the specification and claims to skin. The method can also comprise identifying a person in need of treating hyperpigmentation. Additional methods contemplated by the inventor include methods for reducing the appearance of an age spot, a skin discoloration, or a freckle, reducing or preventing the appearance of fine lines or wrinkles in skin, or increasing the firmness of skin. In one instance, the composition includes palmitoyl tetrapeptide-7, methylsilanol mannuronate, *Lactobacillus* ferment, and plant extracts from *Punica granatum, Castanea sativa, Gossypium hirsutum*, and *Euterpe oleracea*.

Also contemplated are kits that include any one of the compositions disclosed throughout the specification and claims. In certain embodiments, the composition is comprised in a container. The container can be a bottle, dispenser, or package. The container can dispense a predetermined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, or an anti-aging product.

The compositions and methods for their use can "comprise," "consist essentially of," or "consist of" any of the ingredients disclosed throughout the specification. For purposes of consisting essentially of means that inclusion of additional ingredients in the compositions do not materially affect the multi-beneficial properties of the combination of palmitoyl tetrapeptide-7, methylsilanol mannuronate, *Lactobacillus* ferment, and plant extracts from *Punica granatum, Castanea sativa, Gossypium hirsutum*, and *Euterpe oleracea*. One such instance would be the inclusion of an ingredient that has a detrimental effect (e.g., reducing the efficacy or stability) on any one of the ingredients identified in the combination.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant. "Pharmaceutically elegant" and/or "cosmetically elegant" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, skin, hair and nails.

A "non-volatile oil" includes those substance that will not evaporate at ordinary or room temperature.

The terms "mixture," "mix," and "mixing" or any variants of these terms, when used in the claims and/or specification includes, stirring, blending, dispersing, milling, homogenizing, and other similar methods. The mixing of the components or ingredients of the disclosed compositions can form into a solution. In other embodiments, the mixtures may not form a solution. The ingredients/components can also exist as undissolved colloidal suspensions.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

While the compositions of the present invention have the ability to treat skin during the daytime, the inventors discovered that a unique combination of skin active ingredients (e.g., palmitoyl tetrapeptide-7, methylsilanol mannuronate, *Lactobacillus* ferment, and plant extracts from *Punica granatum, Castanea sativa, Gossypium hirsutum*, and *Euterpe oleracea*) works surprisingly well in treating skin during the evening hours. This combination of ingredients is designed to work in sync with a person's skin rhythms to help the skin recover/recuperate during sleep.

Skin acts differently during the daylight hours when compared with nighttime hours. During the day, the skin is exposed to a wide variety of environmental facts ranging from UV light, chronic sun exposure, environmental pollutants, chemicals, disease pathologies, smoking, etc. As a result of this exposure, the skin spends a majority of its resources defending and protecting itself during the day. In the evening hours, by comparison, the exposure to such environmental factors is reduced; this is especially true during sleep. Although the skin attempts to recover/heal from the daily stresses during the evening hours, overtime the skin simply cannot keep up. A solution to this problem would be to provide a way to help the skin recover in a more efficient manner during the evening hours.

To this end, Applicant discovered a way to help the skin rejuvinate/replenish the skin during the evening hours by using a unique combination of ingredients that provide key skin benefits. This combination is chemically compatible (i.e., they are able to coexist together without detrimentally affecting their individual skin efficacy abilities) and skin friendly in that the combination does not appear to irritate the skin. This combination includes palmitoyl tetrapeptide-7, methylsilanol mannuronate, *Lactobacillus* ferment, and plant extracts from *Punica granatum, Castanea sativa, Gossypium hirsutum*, and *Euterpe oleracea*. The result of this combination is a superior way to rejuvenate the skin during the evening hours, which ultimately provides for an effective way to treat a wide variety of skin conditions such as firming/toning the skin, increasing the skin's elasticity, reducing the appearance of dark spots or aged spots, evening out the skin's tone, reducing the appearance of fine lines and wrinkles, reducing other signs of premature skin aging, and reducing the appearance of expression lines. This can be achieved through a single cosmetic formulation/product, which has the added benefit of avoiding to have to use multiple products per day at different times per day. Stated another way, the inventor's combination of ingredients along with a dermatologically acceptable vehicle that can hydrate and moisturize the skin results in a single product that produces multiple skin benefits.

These and other aspect of the present invention are described in further detail below.

A. Active Ingredients

As explained above, topical skin care compositions of the present invention can include Hydrolyzed *Myrtus communis* (myrtle) leaf extract, *Cucurbita pepo* (pumpkin) seed extract, *Gossypium hirsutum* (cotton) extract, *Castanea sativa* (chestnut) seed extract, *Euterpe oleracea* (acai) fruit extract, *Punica granatum* (pomegranate) sterols or fruit extract, *Terminalia ferdinandiana* (kakadu plum) fruit extract, *Ferula foetida* (ferula) root extract, *Myriciaria Dubia* (camu camu) fruit extract, Palmitoyl tetrapeptide-3, Monomethylsilanetriol mannuronate, *Lactobacillus* ferment extract, or *Alteromonas* ferment extract, or combinations thereof.

In particular aspects, the combination includes palmitoyl tetrapeptide-7, methylsilanol mannuronate, *Lactobacillus* ferment, and plant extracts from *Punica granatum, Castanea sativa, Gossypium hirsutum*, and *Euterpe oleracea*. As shown in the Examples, this combination is surprisingly effective in treating a wide range of skin conditions and is particularly effective when applied to facial skin during the evening hours. Any one of these ingredients can be obtained from third party sellers.

For instance, *Gossypium hirsutum* (cotton) extract, extract from the cotton plant, can be purchased from Silab (France) under the trade name HELIOMODULINE™, which was used in the Examples.

*Castanea sativa* (chestnut) seed extract, extract from the nut of the chestnut, can be purchased from Silab (France) under the trade name RECOVERINE™ or from Alban Muller (France) under the trade names BOTANICAL CHESTNUT FRUIT™, LIPIDAMI CHESTNUT FRUIT™, or PHYTAMI CHESTNUT™. RECOVERINE™ was used in the Examples.

*Euterpe oleracea* (acai) fruit extract, extract from the fruit of acai, can be purchased from Southern Cross Botanicals Pty Ltd (NSW Australia), Amax NutraSource (USA) under the trade name ACAI FRUIT EXTRACT™, from Assessa-Industria (Brazil) under the trade name FRULIX TF ACAI™, or from Centroflora Group Botucatu (Brazil) under the trade name ACAI BERRY EXTRACT™. *Euterpe oleracea* (acai) fruit extract from Southern Cross Botanicals Pty Ltd (NSW Australia) was used in the Examples.

*Punica granatum* (pomegrannate) fruit extract can be purchased from Active Organics (USA) under the trade names CO ACTIPHYTE OF POMEGRANATE AJ™, CO ACTIPHYTE OF POMEGRANATE GL™, CO ACTIPHYTE OF POMEGRANATE LIPO O™, CO ACTIPHYTE OF POMEGRANATE LIPO RS™, CO ACTIPHYTE OF POMEGRANATE LIPO S™, and CO ACTIPHYTE OF POMEGRANATE LIPO SUN™. *Punica granatum* (pomegrannate) sterols, sterols obtained from pomegrannate fruit and/or seeds, can be purchased from Active Concepts (USA) under the trade name ABS POMEGRANATE STEROLS™. ABS POMEGRANATE STEROLS™ was used in the Examples.

Palmitoyl tetrapeptide-3 (also referred to as palmitoyl tetrapeptide-7), the reaction product of palmitic acid and tetrapepetide-7 (Gly-Gln-Pro-Arg), can be purchased from Sederma (France) under the trade names EYELISS™, HALOXYL™, MATRIXYL 3000™, and RIGIN™. RIGIN™ was used in the Examples.

Monomethylsilanetriol mannuronate (also referred to as methylsilanol mannuronate), the ester of monomethylsilanol and oligomeric mannuronic acid. Monomethylsilanetriol mannuronate can be purchased from Exsymol S.A.M. (Monaco) under the trade name ALGISIUM C™, which was used in the Examples.

*Lactobacillus* ferment extract, which also includes the ferment and/or lysate of *Lactobacillus*, can be the ferment or lysate produced by fermentation of a given product (e.g., fruits, vegetables, trees, shrubs, plants, milk, seaweed, juice, etc.) with *Lactobacillus*. Examples of *Lactobacillus* ferment extracts that can be used in the context of the present invention include those sold by Active Concepts (USA) under the trade names AC DERMAPEPTIDE LIGHTENING™, ACB MUSTARD BIOFERMENT™, AC DERMAPEPTIDE WARMING OS™, ACB RED CLOVER BIOFERMENT™, ACB COCOA BIOFERMENT™, ACB DATE PALM EXTRACT™, ACB MODIFIED YERBA SANTA GLYCOPROTEIN™, ACB YERBA SANTA GLYCOPROTEIN™, AC YERBA SANTA GLYCOPROTEIN CONCENTRATION™, AC PROBIOTIC 1™, ACB MUSHROOM EXTRACT POWDER™ ACB MUSHROOM EXTRACT SM™, ACB GINSENG BIOFERMENT™, ACB SEA KELP BIOFERMENT™, ACB LEMON PEEL EXTRACT™, ACB YOGURT DERMA RESPIRATORY FACTOR CT™, ACB OAT EXTRACT BETA™, ACB OLIVE LEAF EXTRACT™, ACB PAPYA ENZYME EXTRACT™, ACB PUMPKIN ENZYME™, ACB PUMPKIN ENZYME EF™, ACB MODIFIED PUMPKIN ENZYME™, ACB POMEGRANATE ENZYME™, ACB QUINOA EXTRACT™, ACB TOMATO BIOFERMENT™, ACB LYCOPERSICUM BIOFERMENT™, AC COLORPLEX™, and ACB WATERMELON BIOFERMENT™. In particular embodiments, Active Concepts AC DERMAPEPTIDE LIGHTENING™ can be used for its skin lightening/whitening effects. The AC DERMAPEPTIDE LIGHTENING™, which was used in the Examples, is a *Lactobacillus* ferment lysate filtrate which includes peptides that can help achieve skin lightening/whitening affects.

Hydrolyzed *Myrtus communis* (myrtle) leaf extract, hydrolyzed extract from the leaf of *Myrtus communis*, can be purchased from Silab (France) under the trade name LONGEVICELL™, which was used in the Examples.

*Cucurbita pepo* (pumpkin) seed extract, extract from pumpkin seeds, can be purchased from Draco Natural Products Inc. (USA) under the trade name PUMPKIN EXTRACT™, Naturex (USA) under the trade name PUMPKIN SEED GLYCOLIC EXTRACT™, or from Greentech S.A. (France) under the trade names ARP 100™ and ARP 100 Huileux. ARP 100™ was used in the Examples.

*Terminalia ferdinandiana* (kakadu plum) fruit extract, extract obtained from the fruit of the kakadu plum, can be purchased from Southern Cross Botanicals Pty Ltd (NSW, Australia), which was used in the Examples.

*Ferula foetida* (ferula) root extract, which includes extract from the root *Ferula foetida*, can be purchase from Active Concepts (USA) under the trade name ABS FERULA *FOETIDA* EXTRACT™ and from Arch Personal Care Products (USA) under the trade names NAB ASAFETIDA BG™ and NAB ASAFETIDA EXTRACT™. ABS FERULA *FOETIDA* EXTRACT™ was used in the Examples.

*Myrciaria dubia* (camu camu) fruit extract can be purchased from Amax NutraSource (USA) under the trade name CAMU CAMU EXTRACT™ and from Nichirei (Japan) under the trade names CAMU-CAMU EXTRACT B30™ or CAMU-CAMU EXTRACT W™.

*Alteromonas* ferment extract, extract from the product obtained by the fermentation of *Alteromonas macleodii*, can be purchased from Atrium Innovations (Canada) under the trade names ABYSSINE™, ABYSSINE 657™, ABYSSINE GL 70™, and LANACITYN™. ABYSSINE™ was used in the Examples.

Additional information and suppliers of the above-listed ingredients (and the corresponding trade names) can be found in International Cosmetic Ingredient Dictionary Handbook, 12$^{th}$ Edition (2008), which is incorporated by reference. Further, the extracts identified above can be produced by obtaining the corresponding fruit, seed, or leaf, to produce the extract by extraction methods which are known to those of ordinary skill in the art. The inventors also contemplate that other portions of the substrate (e.g., *Myrtus communis* (myrtle), *Cucurbita pepo* (pumpkin), *Gossypium hirsutum* (cotton), *Castanea sativa* (chestnut), *Euterpe oleracea* (acai), *Punica granatum* (pomegranate), *Terminalia ferdinandiana* (kakadu plum), *Ferula foetida* (ferula), and *Myriciaria Dubia* (camu camu)) producing the extract can be used in the compositions and methods of the present invention. Non-limiting examples of the other portions include the whole fruit, whole vegetable, whole plant, whole tree, whole bush, seed, peel, fruit, stem, bark, leaf, root, flower, petal, bulb, sap, etc. These other portions are described in the International Cosmetic Ingredient Dictionary Handbook, 12th Edition (2008), which is incorporated by reference.

Further, a person of ordinary skill in the art would be able to isolate any one of the extracts identified above from parts of the corresponding plant by using any suitable method known in the art. In one non-limiting example, the plant (or any part of the plant such as the leaves, stems, bark, roots, fruit, flowers or flower buds, seeds, seed pods, sap, whole plant, etc.) can be disrupted by mechanical means which results in a puree. The puree is then processed to be substantially free of impurities or undesired solids. The puree can then be poured into a shallow vessel and quickly exposed to low temperature, i.e., flash frozen, for example at −20° C. or lower, preferably under a vacuum for removal of water content (lyophilization). The resultant extract can then be used in the compositions of the present invention. In other aspects, aqueous, alcoholic, or oil based extraction techniques, or combinations thereof, can be used on the whole plant or any part thereof of (e.g., leaves, stems, bark, roots, fruit, flowers or flower buds, seeds, seed pods, sap, whole plant, etc.) to produce an extract. In such a process, the desired part of the plant or the whole plant is crushed up (e.g., blender) and then subjected to a desired solvent (e.g., water, alcohol, water/alcohol, or oil based solvents) to obtain the desired extract. The extract can then be stored in liquid form, lyophilized, or subject to further processing techniques (e.g., heating, cooling, etc.). Extraction processes are well-known to those having ordinary skill in the extract field (e.g., maceration, infusion, percolation, digestion, decoction, hot continuous extraction, aqueous-alcoholic extract, counter current extract, microwave assisted extraction, ultrasound extraction, supercritical fluid extracts, phytonic extract (e.g., with hydro-flouro-carbon solvents), etc.

B. Determining Skin-Type

The primary skin types of humans are normal skin, dry skin, oily skin, and combination skin. Normal skin typically has an even tone, soft, a smooth texture, with no visible pores or blemishes, and no greasy patches or flaky areas.

Dry skin usually has a low level of sebum and can be prone to irritation. The appearance of dry skin is usually a parched look caused by the skin's inability to retain moisture. Oftentimes it feels "tight" and uncomfortable after washing and is prone to chapping, flaking, and cracking. Dry skin can be exacerbated by wind, extremes of temperature and air-conditioning, all of which cause the skin to flake, chap and feel tight. Dry skin typically has a dull appearance.

Oily skin is typically shiny, thick and dull colored. It typically feels oily oily and has coarse pores and pimples and other embarrassing blemishes. Oily skin usually has oil producing sebaceous glands that are overactive and produce more oil than is needed. The oil oozes and gives the skin a greasy shine. The pores are enlarged and the skin has a coarse look.

Combination skin is a combination of both oily and dry skin. Usually, there is a greasy center panel consisting of nose, forehead and chin and a dry panel consisting of cheeks, mouth and the areas around the eyes.

C. Oxygen Radical Absorbance Capacity

Oxygen Radical Absorption (or Absorbance) Capacity (ORAC) is an assay that measures the antioxidant activity of an ingredient or composition. In essence, it can quantify the degree and length of time it takes to inhibit the action of an oxidizing agent such as oxygen radicals that are known to cause damage cells (e.g., skin cells). The ORAC value of the compositions of the present invention can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

D. Compositions of the Present Invention

It is contemplated that the compositions of the present invention can include any of the skin actives or any combination thereof described throughout this specification. In particular aspects, the skin actives can be combined (e.g., palmitoyl tetrapeptide-7, methylsilanol mannuronate, *Lactobacillus* ferment, and plant extracts from *Punica granatum*, *Castanea sativa*, *Gossypium hirsutum*, and *Euterpe oleracea*). The compositions can include any number of combinations of additional ingredients described throughout this specification. The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

The disclosed compositions of the present invention may also include various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

E. Vehicles

The compositions of the present invention can be incorporated into all types of vehicles. Non-limiting examples of suitable vehicles include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, and ointments or by other method or any combination of the forgoing as would be known to one of ordinary skill in the art (Remington's, 1990). Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

It is also contemplated that ingredients identified throughout this specification, including but not limited to Hydrolyzed *Myrtus communis* (myrtle) leaf extract, *Cucurbita pepo* (pumpkin) seed extract, *Gossypium hirsutum* (cotton) extract, *Castanea sativa* (chestnut) seed extract, *Euterpe oleracea* (acai) fruit extract, *Punica granatum* (pomegranate) sterols or fruit extract, *Terminalia ferdinandiana* (kakadu plum) fruit extract, *Ferula foetida* (ferula) root extract, *Myriciaria Dubia* (camu camu) fruit extract, Palmitoyl tetrapeptide-3, Monomethylsilanetriol mannuronate (also referred to as methylsilanol mannuronate), *Lactobacillus* ferment extract, or *Alteromonas* ferment extract, or any combinations thereof, can be individually or combinatorially encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed-examples include nanospheres and nanocapsules) that can be used as delivery vehicles to deliver the ingredient to skin (see, e.g., U.S. Pat. Nos. 6,387,398; 6,203,802; 5,411,744; Kreuter 1998).

F. Cosmetic Products and Articles of Manufacture

The composition of the present invention can also be used in many cosmetic products including, but not limited to, sunscreen products, sunless skin tanning products, hair products, finger nail products, moisturizing creams, skin benefit creams and lotions, softeners, day lotions, gels, ointments, foundations, night creams, lipsticks, cleansers, toners, masks, or other known cosmetic products or applications. Additionally, the cosmetic products can be formulated as leave-on or rinse-off products. In certain aspects, the compositions of the present invention are stand-alone products.

G. Additional Ingredients

In addition to the Hydrolyzed *Myrtus communis* (myrtle) leaf extract, *Cucurbita pepo* (pumpkin) seed extract, *Gossypium hirsutum* (cotton) extract, *Castanea sativa* (chestnut) seed extract, *Euterpe oleracea* (acai) fruit extract, *Punica granatum* (pomegranate) sterols or fruit extract, *Terminalia ferdinandiana* (kakadu plum) fruit extract, *Ferula foetida* (ferula) root extract, *Myriciaria Dubia* (camu camu) fruit extract, Palmitoyl tetrapeptide-3, Monomethylsilanetriol mannuronate (also referred to as methylsilanol mannuronate), *Lactobacillus* ferment extract, and/or *Alteromonas* ferment extract ingredients disclosed throughout this specification, compositions of the present invention can include additional ingredients such as cosmetic ingredients and pharmaceutical active ingredients. Non-limiting examples of these additional ingredients are described in the following subsections.

I. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, *Ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate). Non-limiting examples of some of these ingredients are provided in the following subsections.

a. UV Absorption Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutyiphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloe-barbadensis extract, aloe barbadensis gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamon (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, matricaria (*Chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (butyrospermum parkii), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

h. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

i. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antip soriatic agents, anti seborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

H. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Nighttime Complex

A combination of skin active ingredients comprising palmitoyl tetrapeptide-7, methylsilanol mannuronate, *Lactobacillus* ferment, and plant extracts from *Punica granatum, Castanea sativa, Gossypium hirsutum*, and *Euterpe oleracea* was tested to determine its efficacy in toning/firming skin, reducing the appearance of fine lines and wrinkles, and hydrating and moisturizing skin. The inventors discovered that this combination of skin actives are chemically compatible and produce a multi-functional product that does not individually require large amounts of these ingredients. It is thought that these low amounts synergistically work together to create the multi-functional product. These ingredients were placed into dermatologically acceptable vehicles that were formulated for normal and dry skin types and for combination and oil skin types. The compositions are provided in Table 1.

TABLE 1*

| Ingredient | Combo/Oily (%) | Normal/Dry (%) |
|---|---|---|
| Skin Actives** | | |
| *Lactobacillus* Ferment | 0.9 | 0.9 |
| *Euterpe Oleracea* Fruit Extract | 0.01 | 0.01 |
| Palmitoyl Tetrapeptide-7 | 0.001 | 0.001 |
| *Punica Granatum* Sterols | 1.0 | 1.0 |
| *Castanea Sativa* Seed Extract | 0.05 | 0.05 |
| *Gossypium Hirsutum* Extract | 0.02 | 0.02 |
| Methylsilanol Mannuronate | 0.01 | 0.01 |
| Vehicle | | |
| Water | 72.1 | 60.8 |
| Glycerin | 4.3 | 8.3 |
| Butylene Glycol | 9.0 | 3.0 |
| Glyceryl Stearate | 1.2 | 1.3 |
| Caprylic/Capric Triglyceride | 4.0 | 3.0 |
| Hydrogenated Polydecene | 1.8 | 4.0 |
| Filler*** | q.s | q.s |

*Add vehicle ingredients to beaker and heat to 70-75° C. while mixing. Subsequently, add the skin actives and cool to 30° C. with mixing.
**A wide variety of commercial suppliers are available for these ingredients and are contemplated for use in the present invention. The particular non-limiting suppliers of each ingredient used to obtain the data for the Table 1 formulations are identified above in the body of the specification.
***Filler ingredients can be used to modify the tactile properties of the composition (e.g., viscosity, substantivety, texture, color, fragrance, etc.) to achieve a desired result.

The composition formulated for combo and oily skin was a cream with medium viscosity. The texture was smooth and creamy. The color was opaque. The scent was neutral or fragrance-free. The after feel was non-greasy.

The composition formulated for normal to dry skin was a gel/cream with a thin viscosity. The texture was smooth and light. The color was opaque. The scent was neutral or fragrance-free. The after feel was non-greasy.

The composition formulated for combo and oily skin was tested on 66 panelists having self-classified combination or oily skin types. The composition formulated for normal or dry skin was tested on 63 panelists having self-classified normal or dry skin types. Panelists were females aged between 32-65 years old having self-perceived mild to moderate fine lines/wrinkles on face. The testing parameters included daily topical application of the composition to the face in the evening and removal in the morning over a period of 12 weeks. Panelists did not use any other skin treatment products during the testing period.

At the end of the 12 week period, a significant majority (average of 75%) of the panelist population agreed that the composition designed for combination and oily skin types: hydrated the skin; fortified the skin; toned the skin; restored skin luminosity; visibly reduced the appearance of fine lines and wrinkles; made the skin feel firmer in areas prone to sagging; lifted the skin from within; recovered/increased elasticity of the skin; made the skin appear more youthful; made the skin appear younger; reduced the appearance of environmental damage to skin; reduced the signs of premature aging; evened skin tone; reduced the appearance of expression lines; reduced the appearance of dark spots; and noticeably contoured the skin.

At the end of the 12 week period, a significant majority (average of 81%) of the panelist population agreed that the composition designed for normal and dry skin types: hydrated the skin; fortified the skin; toned the skin; restored skin luminosity; reduced the appearance of environmental damage to skin; recovered/increased skin elasticity; visibly reduced the appearance of fine lines and wrinkles; made the skin look younger; reduced signs of premature skin aging; made the skin feel firmer in areas prone to sagging; made the skin appear more youthful; reduced the appearance of expression lines; lifted the skin from within; evened the skin tone; and reduced the appearance of dark spots.

For the combination to oily composition, an average of 93% of the panelists agreed that the composition: applied easily and evenly to skin; had a smooth and lightweight feel on the skin; absorbed quickly on the skin; had a non-oily or non-greasy feel; had a rich and luxurious feel.

For the normal to dry composition, an average of 91% of the panelists agreed that the composition: applied easily and evenly to skin; had a smooth and lightweight feel on the skin; absorbed quickly on the skin; had a non-oily or non-greasy feel; had a rich and luxurious feel.

Example 2

Testing Vehicles

In addition to the Table 1 formulations, other non-limiting examples of compositions of the present invention are described in Tables 2 and 3. These compositions can be used as vehicles to test the efficacy of the active ingredients to treat skin.

TABLE 2*

| Ingredient | % Concentration (by weight) |
|---|---|
| Phase A | |
| Water | q.s. to 100 |
| Xanthum gum | 0.1 |

TABLE 2*-continued

| Ingredient | % Concentration (by weight) |
|---|---|
| M-paraben | 0.15 |
| P-paraben | 0.1 |
| Citric acid | 0.01 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C | |
| Active Ingredients** | 2.0 |

*Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.
**Any of the active ingredients (or combination thereof) described in the specification can be used. For instance, the active ingredients can include Hydrolyzed *myrtus communis* (myrtle) leaf extract, *Cucurbita pepo* (pumpkin) seed extract, *Gossypium irsutum* (cotton) extract, *Castanea sativa* (chestnut) seed extract, *Euterpe oleracea* (acai) fruit extract, *Punica granatum* (pomegranate) sterols or fruit extract, *Terminalia ferdinandiana* (kakadu plum) fruit extract, *Ferula foetida* (ferula) root extract, *Myriciaria Dubia* (camu camu) fruit extract, Palmitoyl tetrapeptide-3, Monomethylsilanetriol mannuronate (also referred to as methylsilanol mannuronate), *Lactobacillus* ferment extract, or *Alteromonas* ferment extract, or any combinations thereof. Although the total amount of active ingredients in the Table 1 formulation is 2% w/w, it is contemplated that the amount of active ingredients can be increased or decreased to achieve a desired result, where the water amount can be increased/decreased accordingly (e.g., q.s.).

TABLE 3*

| Ingredient | % Concentration (by weight) |
|---|---|
| Phase A | |
| Water | q.s. to 100 |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C | |
| Active Ingredient(s)** | 2.0 |

*Add ingredients in phase A to beaker and heat to 70-75° C. while mixing. Subsequently, add the phase B ingredient with phase A and cool to 30° C. with mixing. Subsequently, add phase C ingredient while mixing.
**Any of the active ingredients (or combination thereof) described in the specification can be used. For instance, the active ingredients can include Hydrolyzed *myrtus communis* (myrtle) leaf extract, *Cucurbita pepo* (pumpkin) seed extract, *Gossypium hirsutum* (cotton) extract, *Castanea sativa* (chestnut) seed extract, *Euterpe oleracea* (acai) fruit extract, *Punica granatum* (pomegranate) sterols or fruit extract, *Terminalia ferdinandiana* (kakadu plum) fruit extract, *Ferula foetida* (ferula) root extract, *Myriciaria Dubia* (camu camu) fruit extract, Palmitoyl tetrapeptide-3, Monomethylsilanetriol mannuronate (also referred to as methylsilanol mannuronate), *Lactobacillus* ferment extract, or *Alteromonas* ferment extract, or any combinations thereof. Although the total amount of active ingredients in the Table 1 formulation is 2% w/w, it is contemplated that the amount of active ingredients can be increased or decreased to achieve a desired result, where the water amount can be increased/decreased accordingly (e.g., q.s.).

Example 3

Non-Limiting Product Formulations

Additional non-limiting skin product formulations of the present invention are described in Tables 4-6. The compositions can be made by any known methods in the art. For instance, simple mixing of the ingredients into a container can be used. Further, it is contemplated that additional ingredients can be added to the product formulations, listed ingredients can be replaced, and/or listed ingredients can be removed. The concentration ranges of the ingredients can be modified.

TABLE 4*

(Night Moisturizer)

| Ingredient | % Concentration (by weight) |
|---|---|
| Water | qs to 100 |
| Glycerin | 4.0 |
| Butylene Glycol | 8.0 |
| Sodium Polyacrylate | 0.5 |
| Disodium EDTA | 0.05 |
| Caprylic/Capric Triglyceride | 4.0 |
| Cyclomethicone | 1.0 |
| Glyceryl Stearate | 1.2 |
| Dimethicone, 200 cs | 0.5 |
| Cetearyl Alcohol | 0.6 |
| C12-22 Alcohols | 0.4 |
| C12-20 Alkyl Glucoside | 0.1 |
| Preservative | qs |
| Actives** | 0.01-3.0 |
| Additional Ingredients | q.s. to 100% |

*Formulated as an oil-in-water emulsion. Additional ingredients can be added to this formula. For instance, the formula can include: (i) 2 to 5% by weight of denatured alcohol; (ii) 1 to 3% by weight of behenyl alcohol; (iii) 1 to 3% by weight of nylon-12; (iv) 1 to 3% by weight of ethylene/acrylic acid copolymer; (v) 0.1 to 2% by weight of glyceryl stearate; (vi) 0.1 to 2% by weight of aluminum starch octenylsuccinate; and (vii) a combination of *Cucurbita pepo* (pumpkin) seed extract, *Lactobaccillus* ferment extract, *Terminalia ferdinandiana* (kakadu plum) fruit extract, *Myriciaria Dubia* (camu camu) fruit extract, Hydrolyzed *myrtus communis* (myrtle) leaf extract, *Alteromonas* ferment extract, and *Ferula foetida* (ferula) root extract.
**Mixture of *Euterpe oleracea* (acai) fruit extract and Palmitoyl tetrapeptide-7 (from Sederma (France)-RIGIN ™).

TABLE 5*

(Day Lotion w/SPF)

| Ingredient | % Concentration (by weight) |
|---|---|
| Water | qs to 100 |
| Glycerin | 4.0 |
| Butylene Glycol | 2.0 |
| Disodium EDTA | 0.05 |
| Acrylates Copolymer | 2.0 |
| Polyacrylamide | 0.6 |
| Glyceryl Stearate and PEG-100 Stearate | 1.75 |
| Cetyl Alcohol | 1.75 |
| C13-14 Isoparaffin | 0.30 |
| Laureth-7 | .08 |
| Cetearyl Alcohol | 0.65 |
| Ceteth-20 Phosphate | 0.45 |
| Dicetyl Phosphate | 0.2 |
| Homosalate | 10.0 |
| Dimethicone, 200 cs. | 0.75 |
| Octisalate | 5.0 |
| Oxybenzone | 4.5 |
| Avobenzone | 3.0 |
| Preservative | qs |
| Actives** | 0.01 to 3.0 |
| Additional Ingredients | q.s. to 100 |

*Formulated as an oil-in-water emulsion. Additional ingredients can be added to this formula. For instance, the formula can include: (i) 2 to 5% by weight of denatured alcohol; (ii) 1 to 3% by weight of behenyl alcohol; (iii) 1 to 3% by weight of ethylene/acrylic acid copolymer; (iv) 0.1 to 2% by weight of glyceryl stearate; (v) 0.1 to 2% by weight of aluminum starch octenylsuccinate; and (vi) a combination of *Cucurbita pepo* (pumpkin) seed extract, *Lactobaccillus* ferment extract, *Terminalia ferdinandiana* (kakadu plum) fruit extract, *Myriciaria Dubia* (camu camu) fruit extract, Hydrolyzed *myrtus communis* (myrtle) leaf extract, *Alteromonas* ferment extract, and *Ferula foetida* (ferula) root extract.
**Mixture of *Euterpe oleracea* (acai) fruit extract and Palmitoyl tetrapeptide-7 (from Sederma (France)-RIGIN ™).

TABLE 6*

(Cleanser)

| Ingredient | % Concentration (by weight) |
|---|---|
| Water | qs to 100 |
| Glycerin | 25.0 |
| Cocamidopropyl Betaine | 15.0 |
| Potassium Myristate | 7.0 |
| Stearic Acid | 1.5 |

TABLE 6*-continued (Cleanser)

| Ingredient | % Concentration (by weight) |
|---|---|
| Disodium EDTA | 0.1 |
| Triethanolamine | 0.25 |
| Preservative | qs |
| Actives** | 0.01 to 3.0 |
| Additional Ingredients | q.s. to 100 |

*Formulated as a soap. Additional ingredients can be added to this formula. For instance, the formula can include: (i) 2 to 5% by weight of potassium laurate; (ii) 2 to 5% by weight of myristic acid; (iii) 2 to 5% by weight of sodium myristoyl glutamate; (iv) 1 to 3% by weight of PEG-32; (v) 1 to 3% by weight of sorbitol; (vi) 1 to 3% by weight of glyceryl stearate; and (vii) a combination of *Terminalia ferdinandiana* (kakadu plum) fruit extract, *Myriciaria Dubia* (camu camu) fruit extract, and Hydrolyzed *myrtus communis* (myrtle) leaf extract.
**Mixture of *Euterpe oleracea* (acai) fruit extract and Palmitoyl tetrapeptide-7 (from Sederma (France)-RIGIN ™).

Example 4

Non-Limiting Delivery Vehicles

A non-limiting delivery vehicle for skin active ingredients disclosed throughout the specification is described in Tables 7-8. The delivery vehicle can be made by any known methods in the art. For instance, simple mixing of the ingredients into a container can be used. Further, it is contemplated that additional ingredients can be added to the vehicle, listed ingredients can be replaced, and/or listed ingredients can be removed. The concentration ranges of the ingredients can be modified as needed for a given product formulation.

TABLE 7

(Delivery Vehicle)

| Ingredient | % Concentration (by weight) |
|---|---|
| Water | q.s. to 100 |
| Glycerin | 3 to 30 |
| Butylene Glycol | 0.001 to 5 |
| Propylene Glycol | 0.1 to 2 |
| Phenoxyethanol | 0.00001 to 1 |
| Disodium EDTA | 0.01 to 1 |
| Actives* | 0.001 to 5 |
| Additional Ingredients** | q.s. to 100 |

*Any of the skin active ingredients disclosed throughout the specification, or any combination thereof, can be incorporated into this delivery vehicle. Examples of the active ingredients include Hydrolyzed *myrtus communis* (myrtle) leaf extract, *Cucurbita pepo* (pumpkin) seed extract, *Gossypium hirsutum* (cotton) extract, *Castanea sativa* (chestnut) seed extract, *Euterpe oleracea* (acai) fruit extract, *Punica granatum* (pomegranate) sterols or fruit extract, *Terminalia ferdinandiana* (kakadu plum) fruit extract, *Ferula foetida* (*ferula*) root extract, *Myriciaria Dubia* (camu camu) fruit extract, Palmitoyl tetrapeptide-3, Monomethylsilanetriol mannuronate (also referred to as methylsilanol mannuronate), *Lactobacillus* ferment extract, and/or *Alteromonas* ferment extract, or any combinations thereof. In particular embodiments, the skin active ingredients include palmitoyl tetrapeptide, *Euterpe oleracea* (acai) fruit extract, or *Terminalia ferdinandiana* (kakadu plum) extract, or any combination of such ingredients.
**Any of the additional ingredients disclosed throughout the specification, or any combination thereof, can be incorporated into this delivery vehicle.

TABLE 8

(Delivery Vehicle)

| Ingredient | % Concentration (by weight) |
|---|---|
| Water | q.s. to 100 |
| Glycerin | 3 to 30 |
| Butylene Glycol | 0.001 to 5 |
| Propylene Glycol | 0.1 to 2 |
| Phenoxyethanol | 0.00001 to 1 |
| Disodium EDTA | 0.01 to 1 |
| Steareth-20 | 0.0001 to 0.1 |
| Chlorhexidine Diglunonate | 0.00001 to 0.1 |

TABLE 8-continued (Delivery Vehicle)

| Ingredient | % Concentration (by weight) |
|---|---|
| Potassium Sorbate | 0.000001 to 0.1 |
| Preservative (mixture of parabens) | 0.001 to 2 |
| Actives* | 0.001 to 5 |
| Additional Ingredients** | q.s. to 100 |

*Any of the skin active ingredients disclosed throughout the specification, or any combination thereof, can be incorporated into this delivery vehicle. Examples of the active ingredients include Hydrolyzed *myrtus communis* (myrtle) leaf extract, *Cucurbita pepo* (pumpkin) seed extract, *Gossypium hirsutum* (cotton) extract, *Castanea sativa* (chestnut) seed extract, *Euterpe oleracea* (acai) fruit extract, *Punica granatum* (pomegranate) sterols or fruit extract, *Terminalia ferdinandiana* (kakadu plum) fruit extract, *Ferula foetida* (*ferula*) root extract, *Myriciaria Dubia* (camu camu) fruit extract, Palmitoyl tetrapeptide-3, Monomethylsilanetriol mannuronate (also referred to as methylsilanol mannuronate), *Lactobacillus* ferment extract, and/or *Alteromonas* ferment extract, or any combinations thereof. In particular embodiments, the skin active ingredients include palmitoyl tetrapeptide, *Euterpe oleracea* (acai) fruit extract, or *Terminalia ferdinandiana* (kakadu plum) extract, or any combination of such ingredients.
**Any of the additional ingredients disclosed throughout the specification, or any combination thereof, can be incorporated into this delivery vehicle.

Example 5

Supporting Data

The Table 4 moisturizer has been shown to moisturize skin, which is useful in treating a wide range of skin-related conditions (e.g., dry skin, wrinkled skin, aged skin, etc.) (data not included). The Table 5 lotion has also been shown to moisturize skin while also protecting the skin from UV radiation (data not included). The Table 6 formulation has been shown to cleanses skin, which is useful in removing dirt, oil, make-up, and other unwanted substances from skin (data not shown). The Tables 7-8 formulations have been shown to be effective vehicles for the skin active ingredients identified throughout the specification and for use in the Tables 4-6 formulations (data not shown). Each of the Tables 4-8 formulations have also been shown to have excellent tactile properties (i.e., they are "cosmetically elegant").

Example 4

Assays that can be Used to Test Compositions

The efficacy of any one of the compositions disclosed throughout the specification and claims (including, for example, the formulations identified in Tables 1-8), can be determined by methods known to those of ordinary skill in the art. The following are non-limiting assays that can be used in the context of the present invention. It should be recognized that other testing procedures can be used, including, for example, objective and subjective procedures.

Erythema Assay:

An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with a composition of the present invention. Repeat measurements are taken at regular intervals to determine the formula's ability to reduce redness and irritation.

Skin Moisture/Hydration Assay:

Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance.

Skin Clarity and Reduction in Freckles and Age Spots Assay:

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b2)^{1/2}$.

Skin Dryness, Surface Fine Lines, Skin Smoothness, and Skin Tone Assay:

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay:

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical Grading of Skin Smoothness Assay:

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin Smoothness and Wrinkle Reduction Assay with Methods Disclosed in Packman et al. (1978):

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin Firmness Assay with a Hargens Ballistometer:

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer:

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas:

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the are of the replicas covered by wrinkles or fine lines was determined.

Surface Contour of the Skin Assay with a Profilometer/Stylus Method:

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $I_m$=the traverse (scan) length; and y=the absolute value of the location of the profile relative to the mean profile height (x-axis).

MELANODERM™ Assay:

In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

ORAC Assay:

Oxygen Radical Absorption (or Absorbance) Capacity (ORAC) of the aromatic skin-active ingredients and compositions can also be assayed by measuring the antioxidant activity of such ingredients or compositions. This assay can quantify the degree and length of time it takes to inhibit the action of an oxidizing agent such as oxygen radicals that are known to cause damage cells (e.g., skin cells). The ORAC value of the aromatic skin-active ingredients and compositions can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

Matrix Metalloproteinase Enzyme Activity (MMP3; MMP9) Assay:

An in vitro matrix metalloprotease (MMP) inhibition assay. MMPs are extracellular proteases that play a role in many normal and disease states by virtue of their broad substrate specificity. MMP3 substrates include collagens, fibronectins, and laminin; while MMP9 substrates include collagen VII, fibronectins and laminin. Using Colorimetric Drug Discovery kits from BioMol International for MMP3 (AK-400) and MMP-9 (AK-410), this assay is designed to measure protease activity of MMPs using a thiopeptide as a chromogenic substrate (Ac-PLG-[2-mercapto-4-methyl-pentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm (c=13,600 M-1 cm-1 at pH 6.0 and above 7).

All of the skin-active ingredients, compositions, or methods disclosed and claimed in this specification can be made and executed without undue experimentation in light of the present disclosure. While the skin-active ingredients, compositions, or methods of this invention have been described in terms of particular embodiments, it will be apparent to those of skill in the art that variations may be applied to the skin-active ingredients, compositions, or methods and in the steps or in the sequence of steps of the method described herein without departing from the concept, spirit and scope of the invention.

The invention claimed is:

1. A topical skin treatment composition comprising: an effective amount of
   (a) palmitoyl tetrapeptide 7;
   (b) retinol;
   (c) caprylic/capric triglyceride;
   (d) Helianthus Annuus seed oil;
   (e) bisabolol;
   sorbitan laurate;
   (g) polysorbate 20; and
   (h) tocopheryl acetate.

2. The topical skin care composition of claim 1, further comprising: an effective amount of
   (i) sesame oil;
   (j) jojoba oil;
   (k) carthamus tinctorius oil; and
   (l) rose oil.

3. The topical skin care composition of claim 2, wherein the topical skin care composition is anhydrous.

4. The topical skin care composition of claim 1, wherein the topical skin care composition is anhydrous.

5. A method of treating skin, the method comprising topically applying to skin in need thereof, the topical skin care composition of claim 1, wherein topical application of the composition to the skin treats the skin.

6. The method of claim 5, wherein the topical skin care composition is applied to facial skin.

7. The method of claim 5, wherein the topical skin care composition is applied to a fine line or wrinkle.

8. The method of claim 5, wherein the topical skin care composition moisturizes skin.

9. The method of claim 5, wherein the topical skin care composition further comprises: an effective amount of
   (i) sesame oil;
   (j) jojoba oil;
   (k) carthamus tinctorius oil; and
   (l) rose oil.

10. The method of claim 9, wherein the topical skin care composition is anhydrous.

11. The method of claim 5, wherein the topical skin care composition is anhydrous.

* * * * *

UNITED STATES PATENT AND TRADEMARK OFFICE
CERTIFICATE OF CORRECTION

| | |
|---|---|
| PATENT NO. | : 11,123,578 B2 |
| APPLICATION NO. | : 16/556753 |
| DATED | : September 21, 2021 |
| INVENTOR(S) | : Dawn Burke-Colvin, Michelle Hines and David Gan |

Page 1 of 1

It is certified that error appears in the above-identified patent and that said Letters Patent is hereby corrected as shown below:

In the Claims

<u>Claim 1, Column 36, Line 22:</u>
Replace "sorbitan laurate" with -- (f) sorbitan laurate --.

Signed and Sealed this
Eighteenth Day of October, 2022

Katherine Kelly Vidal
*Director of the United States Patent and Trademark Office*